United States Patent [19]

Watanabe et al.

[11] Patent Number: 5,057,429
[45] Date of Patent: Oct. 15, 1991

[54] APPARATUS FOR FLOATING ANIMAL CELLS IN A DOUBLE-BAG CONTAINER

[75] Inventors: Katsuto Watanabe, Hadano; Yoshihiko Nakamura, Isehara; Takashi Noto, Ayase; Masaichi Yamamura, Atsugi; Hitoshi Nakashima, Sagamihara; Kazunori Ichinohe, Sagamihara; Yukitaka Mino, Sagamihara; Kazuhiro Nishijima, Sagamihara, all of Japan

[73] Assignee: Kawasumi Laboratories Inc., Tokyo, Japan

[21] Appl. No.: 349,701

[22] Filed: May 10, 1989

Related U.S. Application Data

[62] Division of Ser. No. 90,226, Aug. 27, 1987.

[30] Foreign Application Priority Data

| Aug. 27, 1986 | [JP] | Japan | 61-198898 |
| Mar. 31, 1987 | [JP] | Japan | 1-46745[U] |
| Apr. 3, 1987 | [JP] | Japan | 1-80991 |
| Jul. 11, 1987 | [JP] | Japan | 1-172101 |

[51] Int. Cl.$^5$ ............................................. C12M 3/02
[52] U.S. Cl. ..................... 435/286; 435/311; 435/316; 604/410; 604/903; 383/37; 206/213.1
[58] Field of Search ............... 435/2, 240.1, 240.22, 435/240.241, 240.25, 284–286, 316, 311; 366/217, 209, 208, 210, 216, 214; 604/408–410, 903; 383/37; 206/205, 213.1; 220/426

[56] References Cited

U.S. PATENT DOCUMENTS

| 2,494,866 | 1/1950 | Fressola | 366/210 |
| 4,183,677 | 1/1980 | De Bruyne | 366/209 |
| 4,293,643 | 10/1981 | Ohtake et al. | 366/214 |
| 4,661,455 | 4/1987 | Hubbard | 435/285 |
| 4,829,002 | 5/1989 | Pattillo et al. | 435/284 |

FOREIGN PATENT DOCUMENTS

| 3248543 | 7/1983 | Fed. Rep. of Germany | 435/284 |
| 1404624 | 5/1965 | France | 604/408 |
| 1530705 | 11/1978 | United Kingdom . | |

Primary Examiner—David L. Lacey
Assistant Examiner—William H. Beisner
Attorney, Agent, or Firm—Michael J. Striker

[57] ABSTRACT

The instant invention relates to an apparatus for floating animal cells in a double-bag container, where an outer bag containing culture media and a volume of air houses an inner bag of a semipermeable film containing cells suspended in a culture media. The semipermeable film has pores of sufficient size so as to prohibit cells within the inner bag from passing therethrough but allowing culture liquid and air to pass through it. To optimize the exchange of nutrients between the interiors of the two bags, a protective mesh surrounds the inner bag and the double-bag container is fastened to an agitator which provides either a rotating or shaking motion.

8 Claims, 12 Drawing Sheets

FIG_1
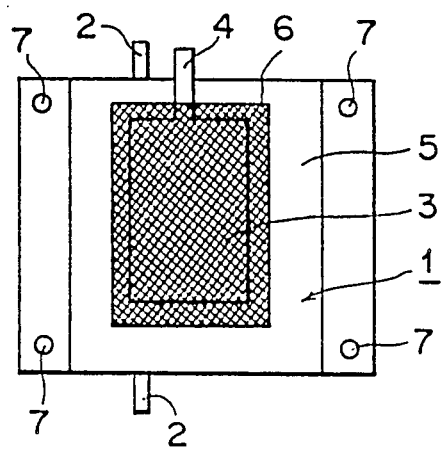
FIG_4
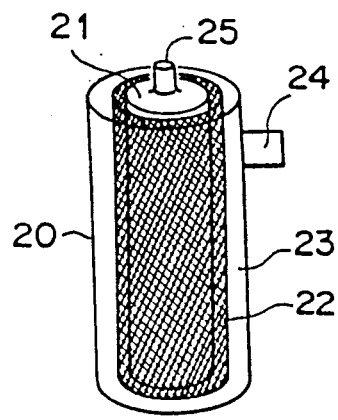
FIG_2
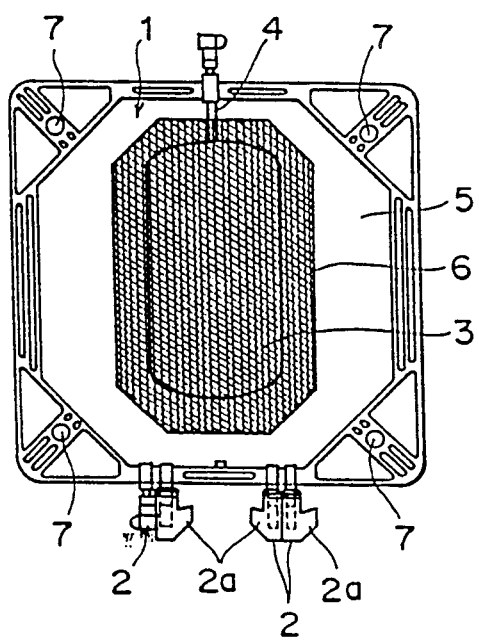
FIG_3(A)
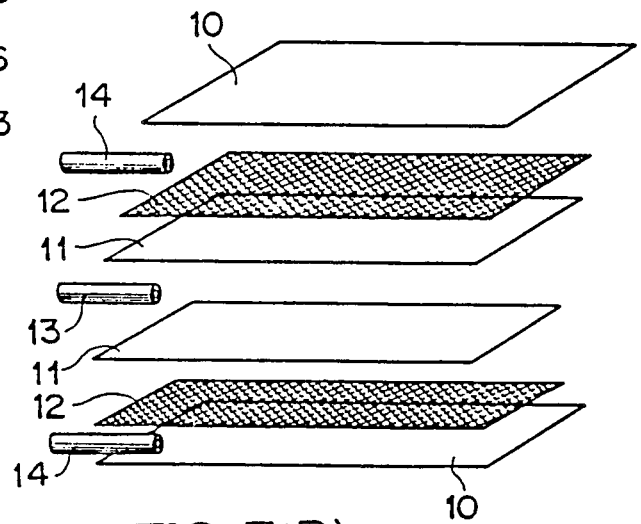
FIG_3(B)
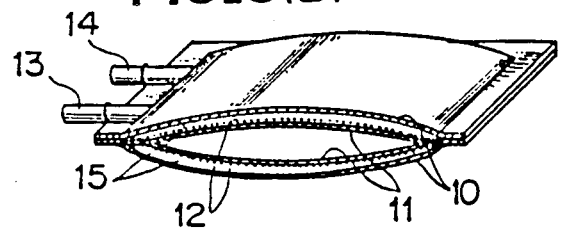

FIG_5(A) FIG_5(B)
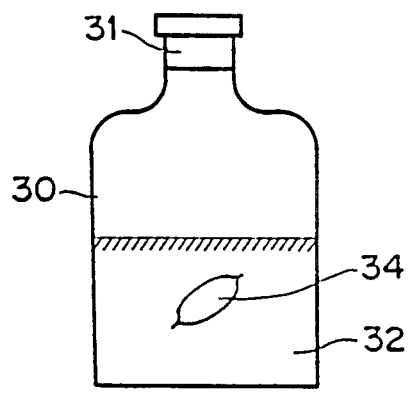
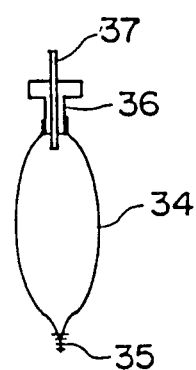
FIG_6
FIG_7
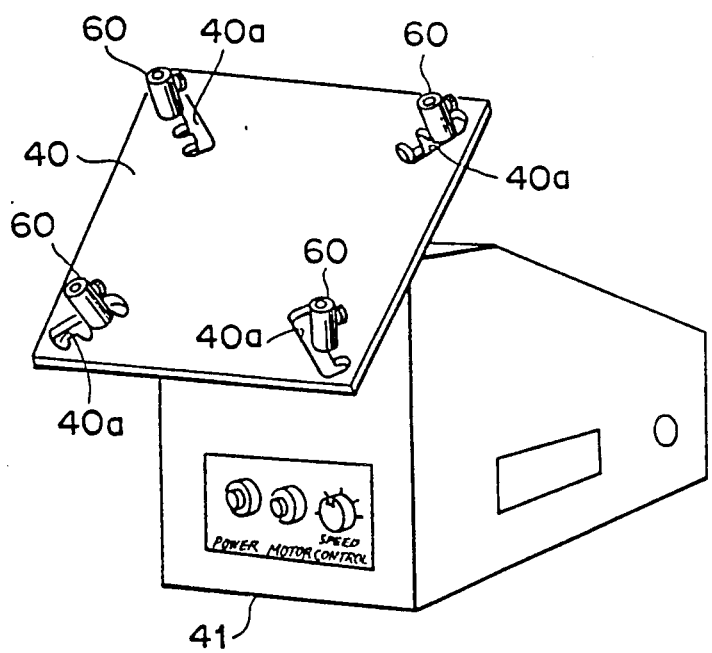
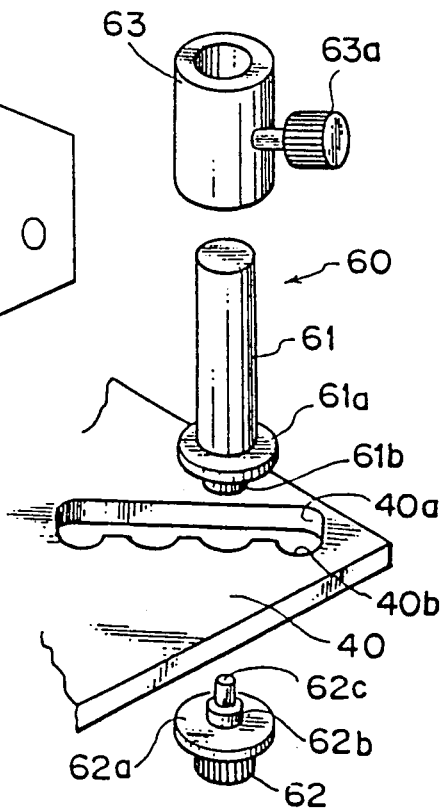

FIG_8
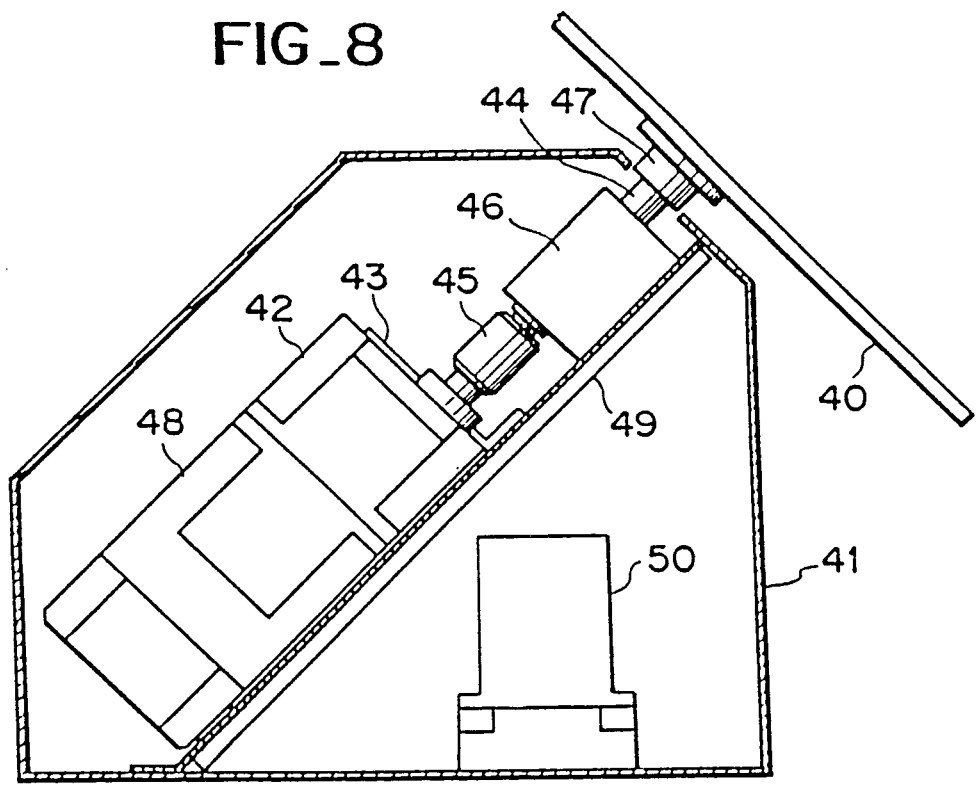
FIG_9
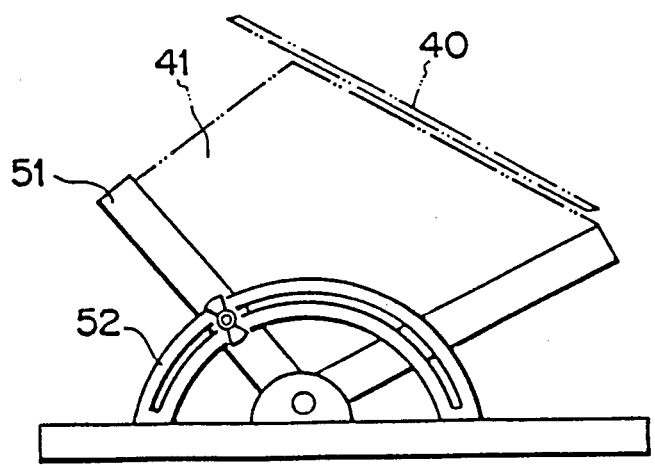

FIG_10
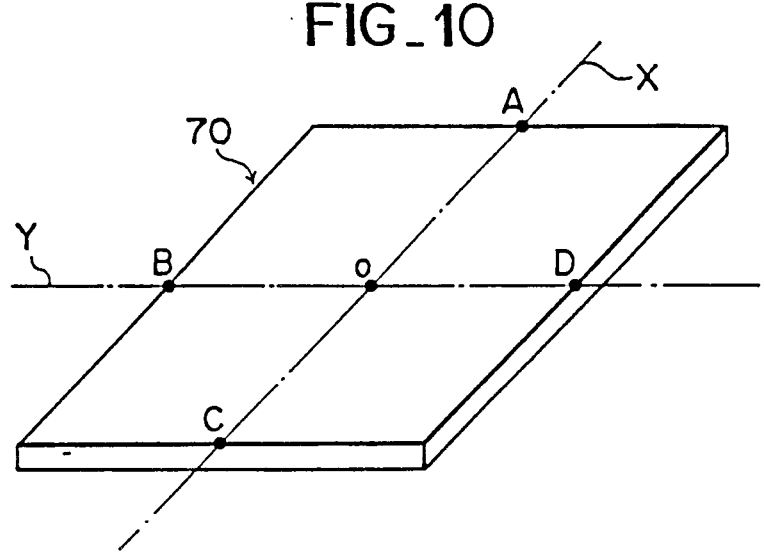
FIG_11
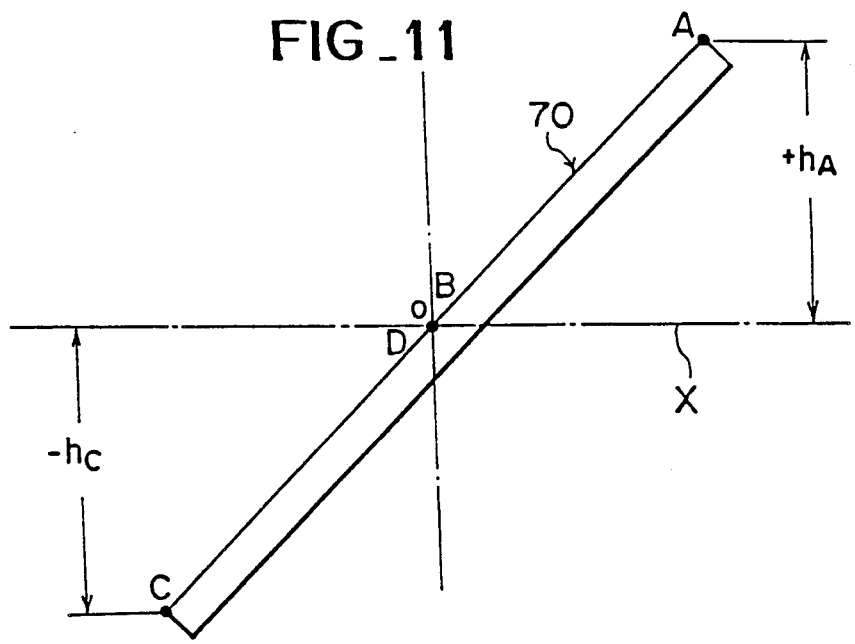
FIG_12
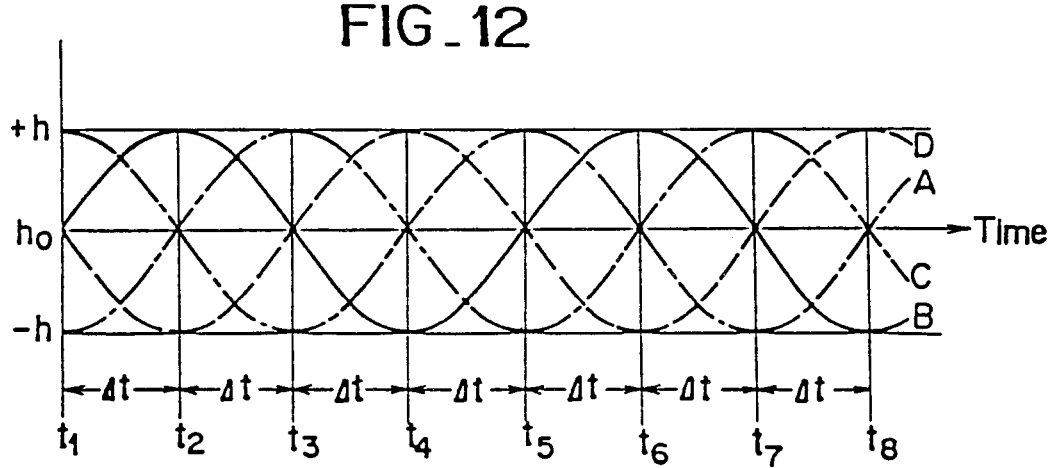

FIG_13
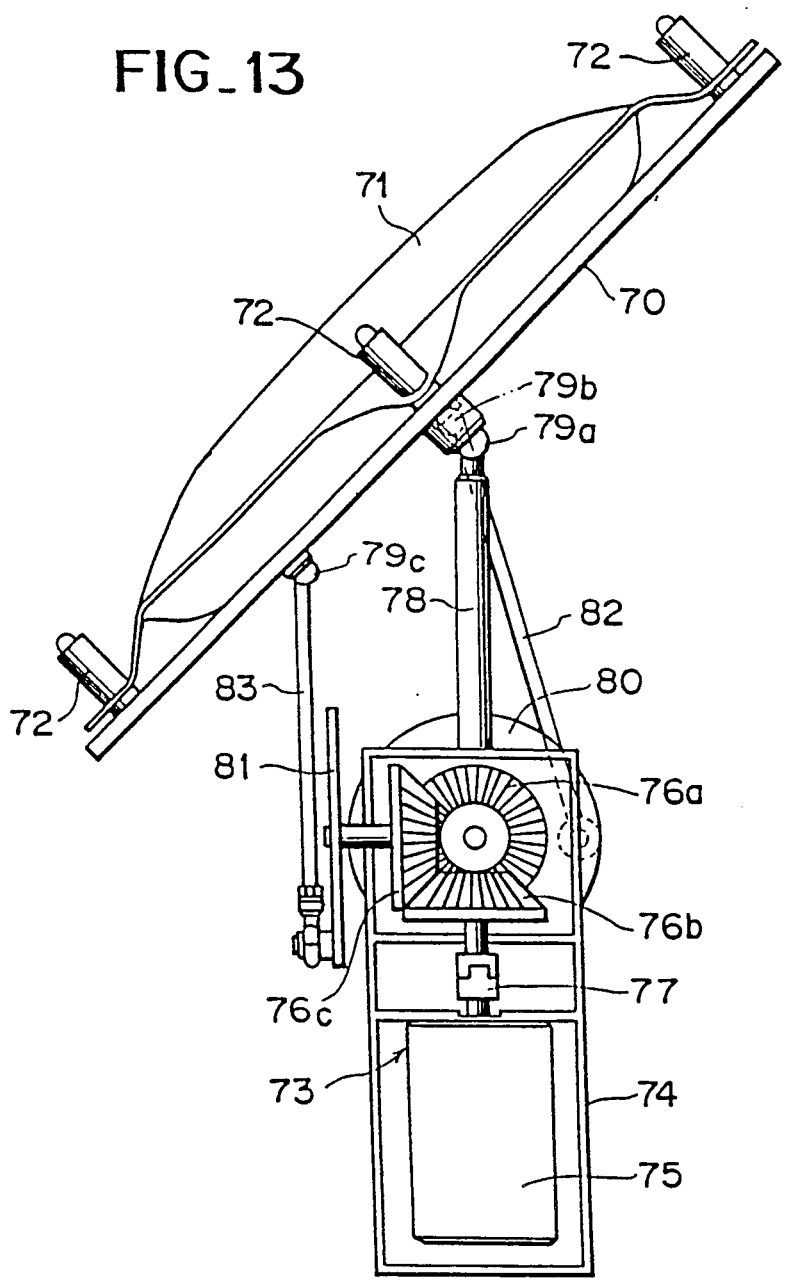
FIG_14
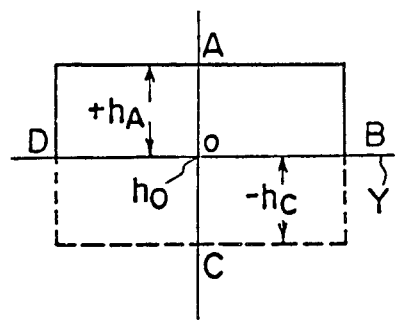
FIG_15
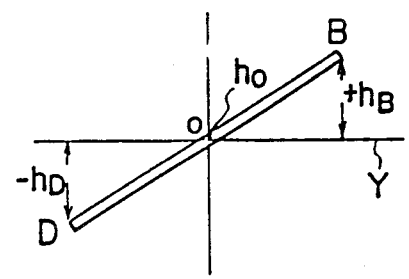

FIG._16
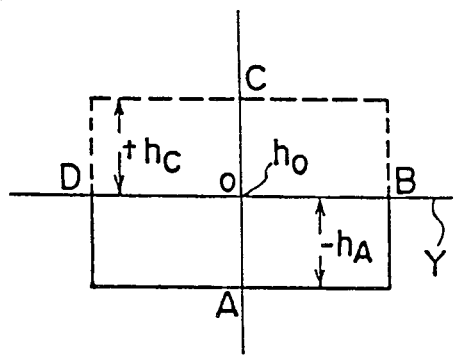
FIG._17
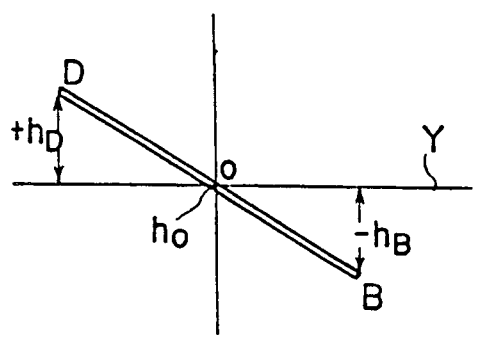
FIG._18(A)
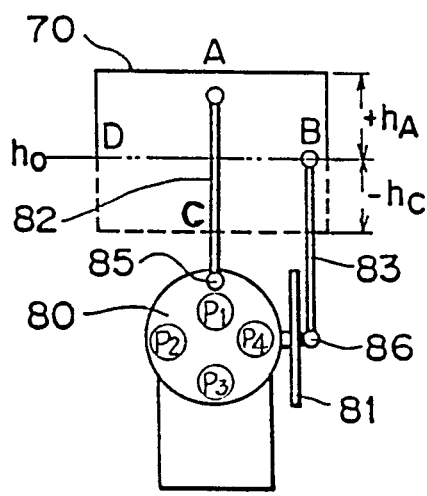
FIG._19(A)
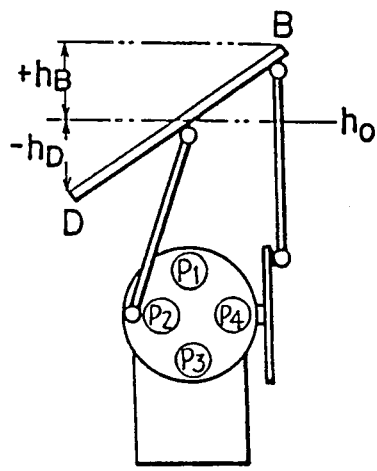
FIG._18(B)
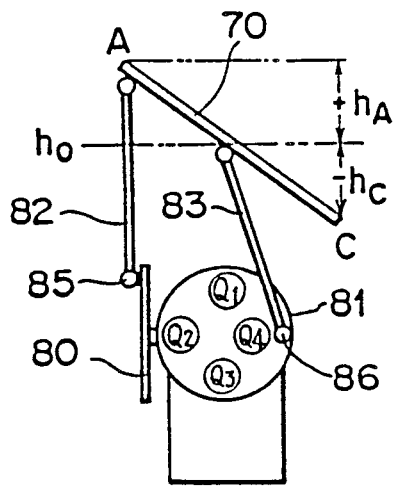
FIG._19(B)
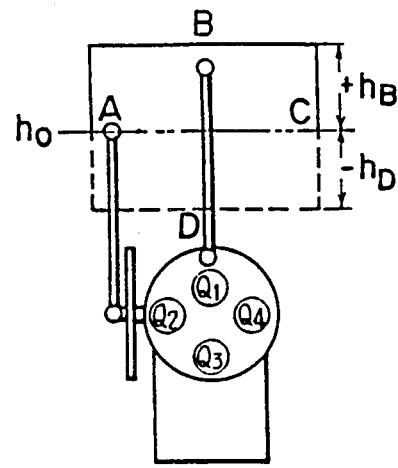

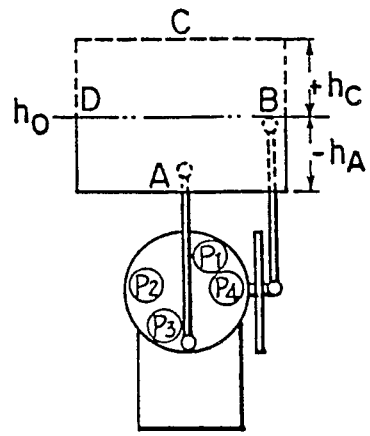
FIG_20(A)
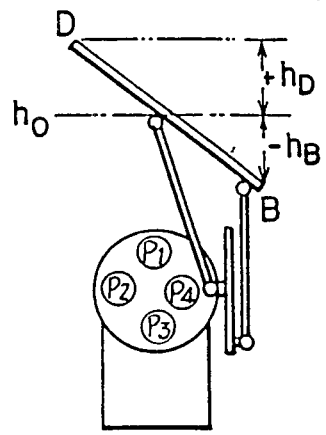
FIG_21(A)
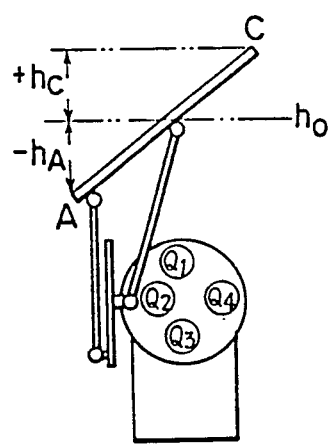
FIG_20(B)
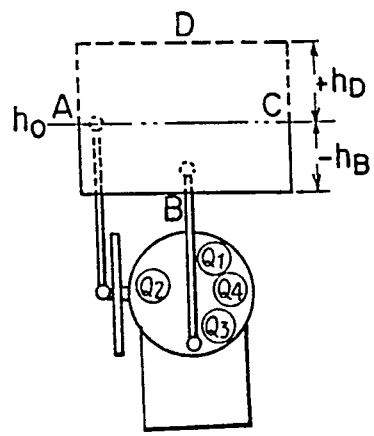
FIG_21(B)
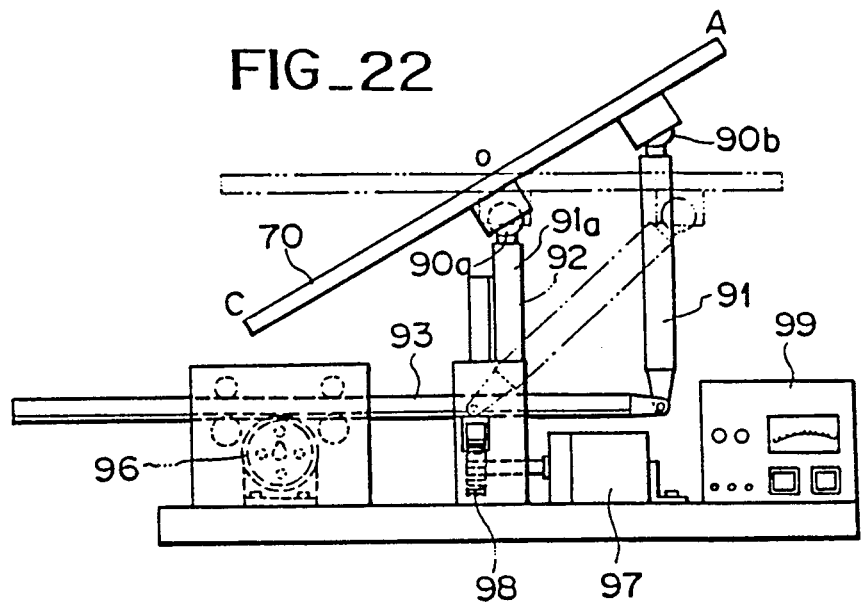
FIG_22

FIG_23
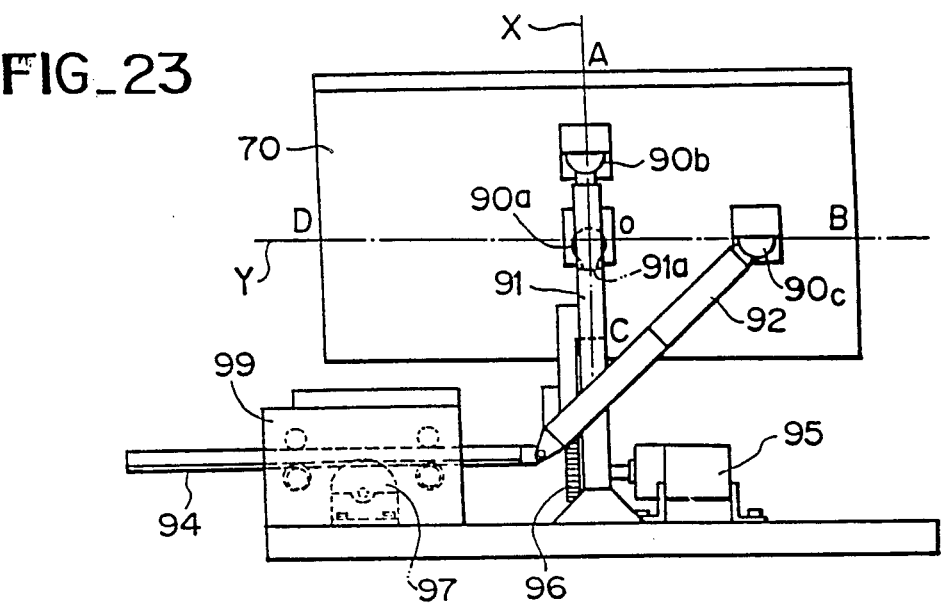
FIG_24
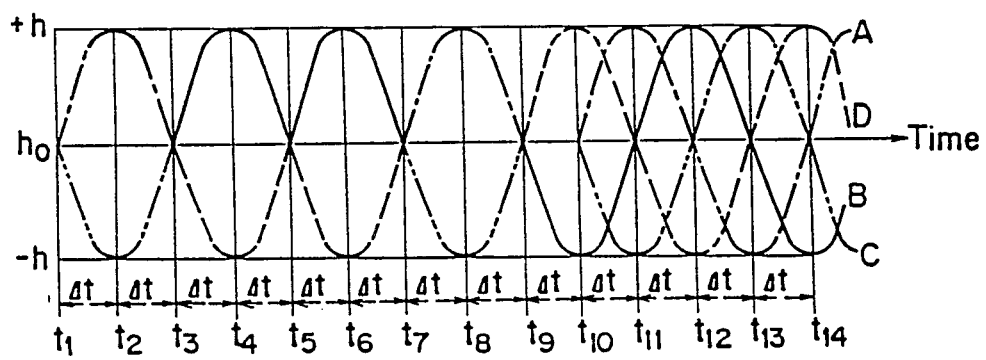
FIG_25
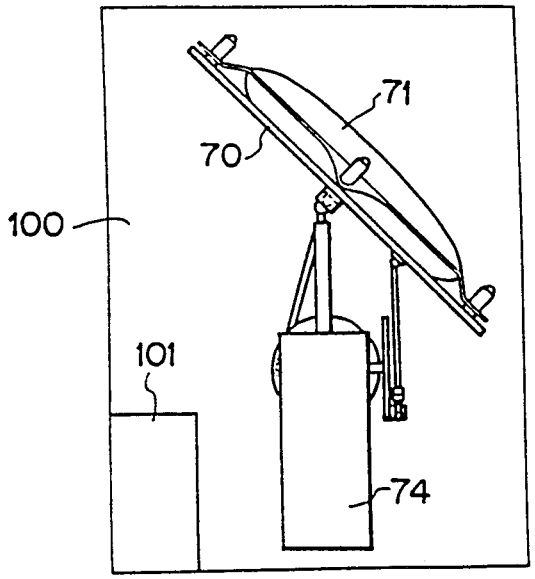

FIG_26
FIG_27
FIG_28
FIG_29
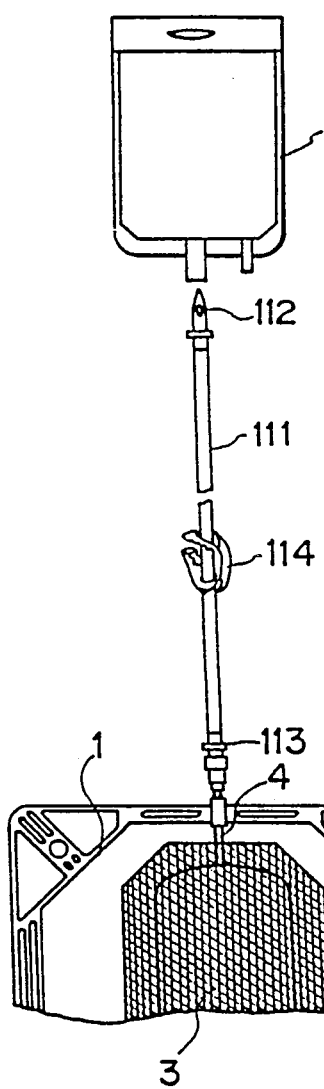
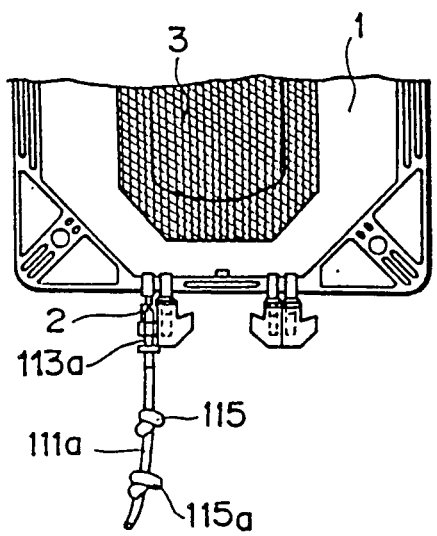
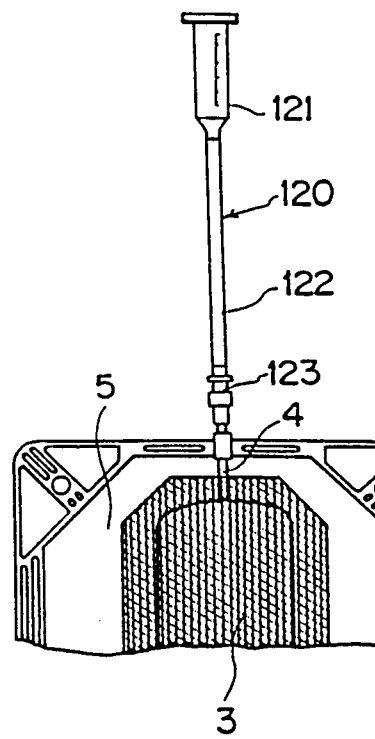
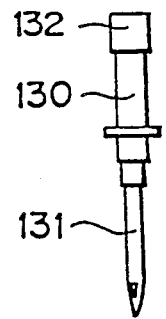

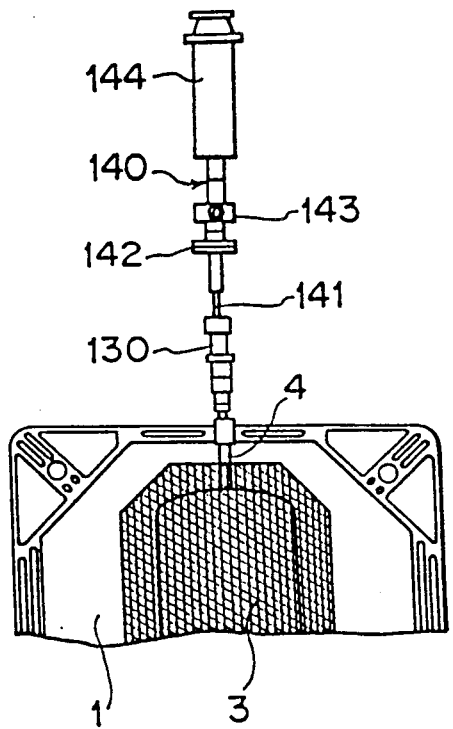
FIG_30
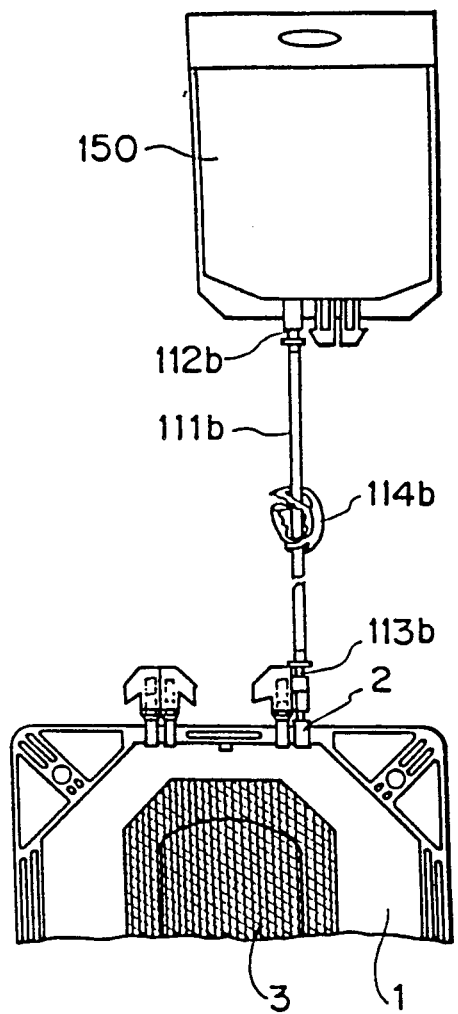
FIG_31
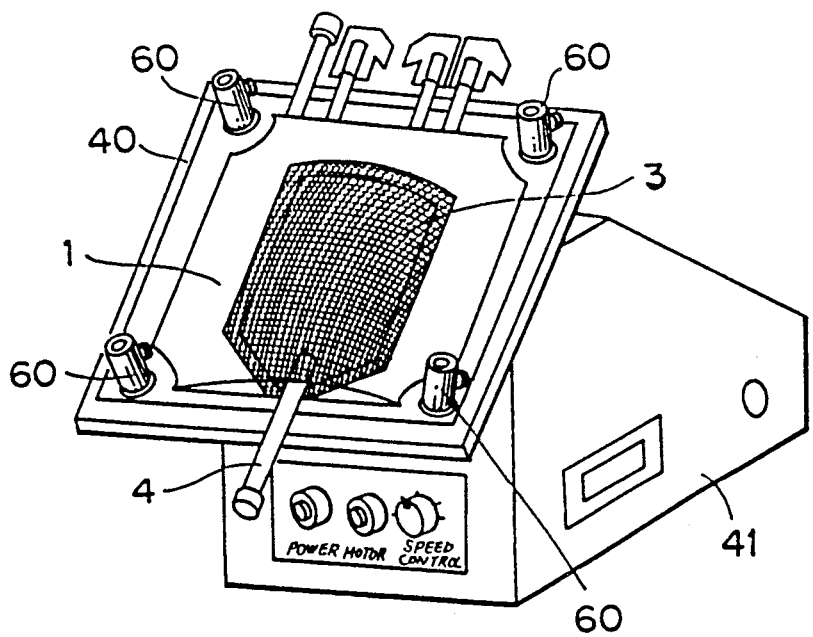
FIG_32

FIG_33
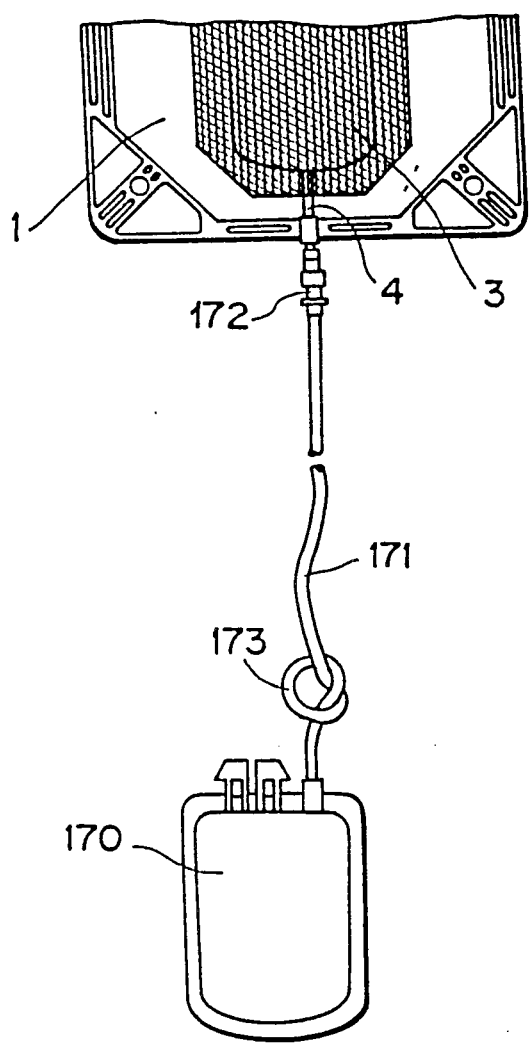
FIG_34
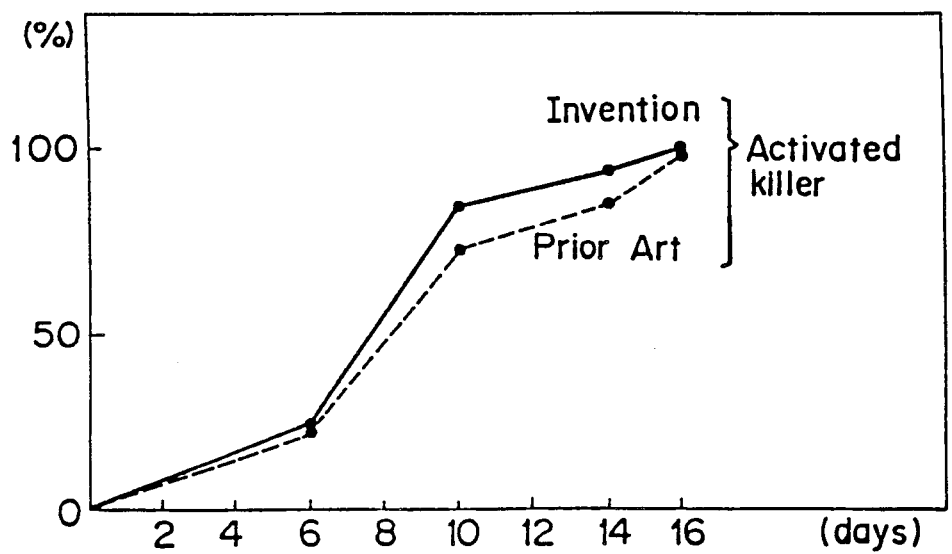

FIG_35
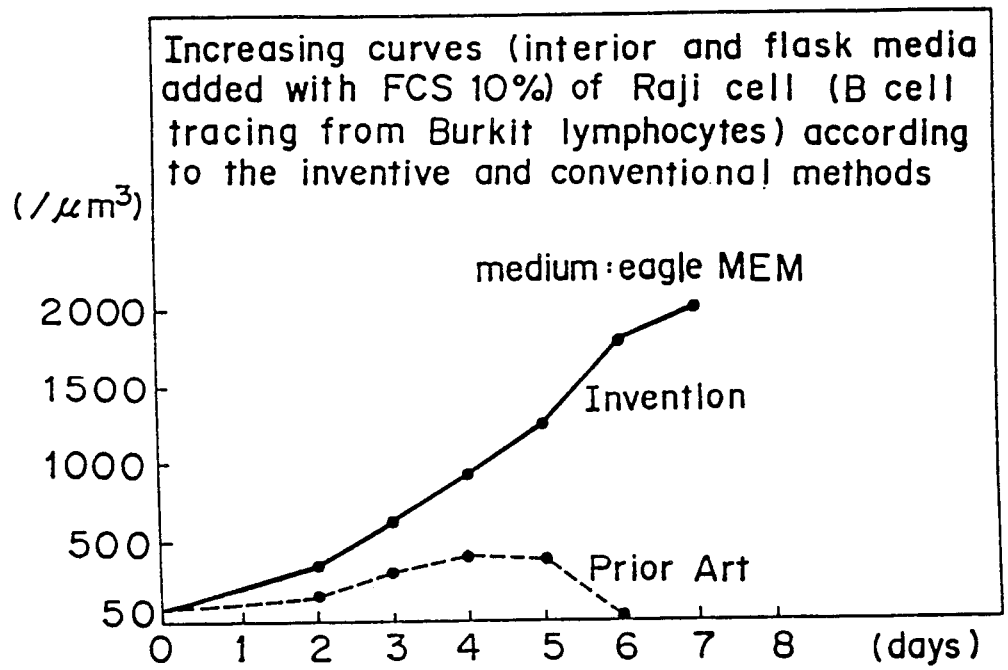
FIG_36
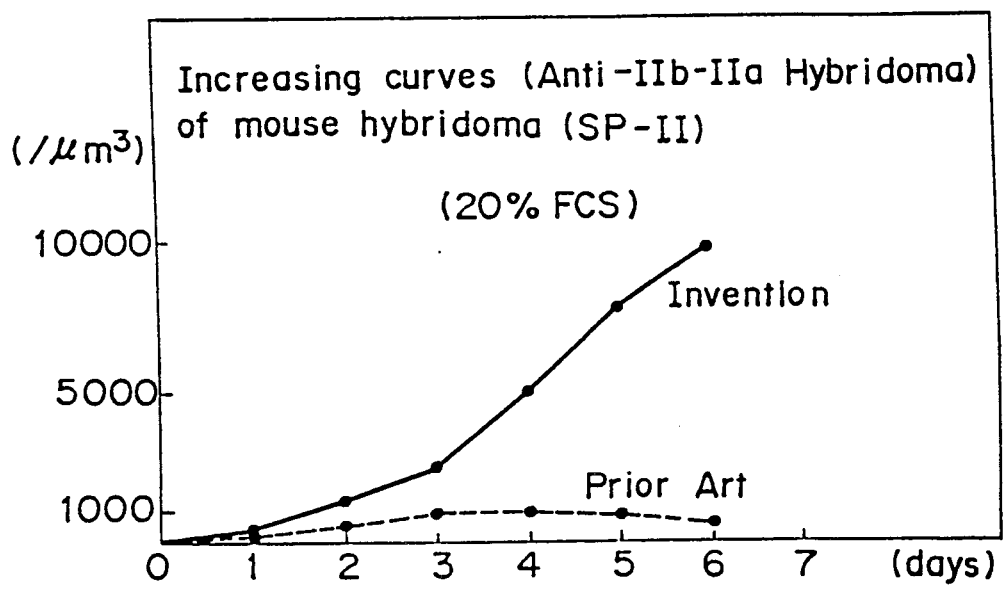

APPARATUS FOR FLOATING ANIMAL CELLS IN A DOUBLE-BAG CONTAINER

CROSS-REFERENCE TO A RELATED APPLICATION

This is a division of application Ser. No. 07/090,116, filed 8/27/87.

BACKGROUND OF THE INVENTION

This invention relates to a method and an instrument for cultivating especially tissue cells at high concentration or high activity.

DESCRIPTION OF THE PRIOR ART

Known cultivating methods for tissue or animal cells are flask cultivation using liquid media; a rotary cell culture which causes the cells to attach to the inner wall of a roller bottle or float them therein; another way which causes the cells to attach to the surfaces of beads and cultivate there; or a further way, which causes the cells to attach to a hollow membrane of a semi-permeable film, and supplies a cultivating liquid to a rear side thereof.

However, with respect to those conventional methods, when culture media for the cells floating in the roller bottle are exchanged, the cells are rendered subside or precipitate by such as a centrifugal operation. This operation is not only troublesome but dangerous because of pollution. Further, the rotary cell culture or the beads attaching ways are difficult in yielding the cells, and requires a provision for a thermostatic chamber or an exclusive incubator. In the hollow membrane of the semi-permeable film, since the cells attach thereto, the yielding is poor, and if the cultivation is required much, the area of the hollow fiber film should be broadened. In addition, An instrument is required for circulating the cultivating liquid and for supplying it, and as a whole the instrument will be of large scale and high cost.

SUMMARY OF THE INVENTION

The present invention has been developed through many investigations to remove problems at tissue in the prior art.

It is an object of the invention to provide a method for cultivating the tissue cells by an effective and economical way at high concentration or high activity.

It is another object of the invention to provide an instrument for practising the present cultivating method efficiently and economically.

For cultivating the tissue cells, the invention encloses the cells within a container of a semi-permeable film together with cultivating media and gas, and retains the media and the gas outside of the semi-permeable film, thereby to culture the cells through the semi-permeable film at high density by the media in the semi-permeable film container as well as diffusion; phenomena caused by a tendency of the media to concentrate outside of said film. It is preferable to culture the cells while rotating or turning the container at angles desirable for the cells.

A cultivating instrument is provided with a container of the semi-permeable film for holding the cells to be cultivated, and with another container for holding the cultivating liquid and the gas outside of said semi transparent film container, as well as a communication between the former and latter containers.

The semi-permeable film may be a cellulose such as re-gene rated cellulose or cellulose acetate, or a film such as polyacrylonitrile, polymethylmethacrylate, polysulfone, polycarbonate, polyamide, polyethylene, polypropylene, ethylenevinylalchole, chitin or chitosan.

Pore sizes depend upon the sizes of the cells or the cultivating liquid, but they are sufficient for passing the cultivating liquid and the gas, not passing the cells when the pore size is, preferably not more than 0.2 $\mu$. If additives are supplied other than the cultivating liquid, the pore sizes should be selected taking the sizes of the additives into consideration (when the additives are given within the semi-permeable film container, the pore size should be selected not to pass the additives, and when they are given to the cultivating liquid outside of the film, the pore size is selected to pass them but not to pass useful products obtained from the cells).

Preferably, a mesh-like cover encircles the semi-permeable film container, and the communication mouth may be plural as required.

While cultivating the cells in said container, the container is rotated or shaked to slowly agitate them, so that the interior liquid and the exterior liquid are effectively contacted with each other through said film, and the cells are avoided from adhering to the inner wall thereof, and the yielding efficiency of the cells may be increased. The agitator comprises a fixing plate for supporting the cultivating container and a rotating or shaking mechanism of the fixing plate. The rotation system is not limited to special angles, but could obtain desired results at any angles of 30°, 45° and 60°.

BRIEF DESCRIPTION OF THE DRAWINGS

FIG. 1 shows an outline of a cultivating container of the present invention;

FIG. 2 shows a cultivating container actually exemplified;

FIG. 3(A) shows another embodiment of a cultivating container of the invention, in a dismantled configuration.

FIG. 3(B) shows the assembled container of FIG. 3(A) in half cross-section.

FIG. 4 shows a perspective view of another embodiment of the container to be used in this invention;

FIG. 5(A) shows a further embodiment of an outline of an outer container.

FIG. 5(B) shows an outline of an inner container as shown in FIG. 5(A).

FIG. 6 shows a whole perspective view of a rotary cell cultivating device which will use the container of the invention;

FIG. 7 shows a dismantled view showing a fixing means of the container in the device of FIG. 6;

FIG. 8 shows an outline for explaining a drive mechanism of the device of FIG. 6;

FIG. 9 shows a side view showing a bed for mounting the rotary cell cultivating device;

FIG. 10 shows an explanatory view for actuating a shaking plate for cultivating the cells while shaking the container;

FIG. 11 shows a side view of FIG. 10;

FIG. 12 shows a graph showing time changing between a center O and heights of A, B, C, D;

FIG. 13 shows an outline of the shaking device for moving the shaking plate at periods of FIG. 12;

FIGS. 14 to 17 shows outlines for explaining actuations of the shaking plate in accordance with the periods of FIG. 12;

FIGS. 18(A), 19(A), 20(A) and 21(A) show outlines actuating changes of the shaking device in response to movements of the shaking plate of FIGS. 14 to 17, where the outlines depict a rear view of FIG. 13.

FIGS. 18(B), 19(B), 20(B) and 21(B) depict a right rear side of FIGS. 18(A), 19(A), 20(A) and 21(A), respectively.

FIG. 22 show an outline of the shaking device for actuating the cultivating container at another period;

FIG. 23 show a right side view of FIG. 22;

FIG. 24 show a graph showing time changing between a center O and heights of A, B, C, D of the shaking plate actuated by the device of FIGS. 22 and 23;

FIG. 25 shows an outline showing cultivation while controlling temperature when the shaking cultivation device is positioned in a sealed chamber;

FIGS. 26 to 33 show outlines for explaining sequences of operating the cultivating instrument of the invention;

FIG. 26 shows an outline for explaining washing of the cultivating container;

FIG. 27 shows an outline of sealing a communicating tube after an outer bag has been washed;

FIG. 28 shows an outline showing connection of a charging instrument of the floating cells in an inner bag;

FIG. 29 shows an adapter to be used in this invention;

FIG. 30 shows an outline showing a connection of the inner bag to a steriled air charging instrument;

FIG. 31 shows an outline of a connection of an outer bag to a culturing bag;

FIG. 32 shows a perspective view showing the container attached to the shaking cultivation device;

FIG. 33 shows an outline of a connection of a cell yielding bag to the inner bag;

FIG. 34 shows a graph showing activated killer of LAK cells by the inventive and conventional methods;

FIG. 35 shows a graph showing increasing curves of Raji cells; and,

FIG. 36 shows a graph showing increasing curves of mouse hybridoma.

DETAILED DESCRIPTION OF PREFERRED EMBODIMENTS OF THE INVENTION

FIG. 1 is an outlined view showing an example of the cultivating container of the invention. A sealing bag made of soft or half hard plastic treated with single layer or laminate of vinyl chloride, ethylene acetate vinyl copolymer, polypropylene, polyethylene, polyester, Teflon or polyamid and communication mouths 2 are provided for charging the cultivating liquid and the gas at upper and lower parts. A mouth once used is sealed so as to not allow re-use.

Within the outer bag 1, a semi-permeable film bag 3 is provided, and a part 5 is formed outside of the bag 3 for holding the cultivating liquid. A communication mouth 4 is projected from the upper part of the outer bag 1 for charging the cells. The semi-permeable film bag 3 is encircled with a protecting mesh cover 6.

The outer bag 1 is composed by sealing two sheets of plastic at their peripheries. The plastic tubes, as the communicating mouth 2, 4, are secured to the bag 1 so as to seal the upper and lower ends thereof, which may be fixed with mouths (corresponding to a blood transfusion mouth to be used for a blood bag). The protecting cover 6 is formed in a bag and holds the half transparent film bag 3 therewithin.

The plastic sheet is formed with holes 7 at four corners for securing when rotation or shaking is effectuated.

FIG. 2 shows a cultivating container made in trial following FIG. 1, and the same numerals are given to the same parts. A difference from FIG. 1 is that mouths 2, 2 communicating with the interior of the outer bag 1 are plural at the lower part of the bag 1. The communication mouths 2, 2 are sealed with protectors 2a.

FIG. 3 shows another example of the cultivating container which is composed by holding two sheets of the half transparent films 11, 11 and two sheets of the outer mesh protecting covers 12, 12 between the outer plastic sheets 10, 10, and positioning the communication mouths 13, 14 between the sheets 11, 11 and between the outer sheet 10 and the protecting cover 12, and melting the peripheries. Thus, the half transparent film bag is enclosed within the bag formed with the sheets 10, 10 and a part 15 is formed for containing the culture liquid and the gas outside of the bag.

FIG. 4 shows a further embodiment of the invention, where an outer sealing case 20 is cylindrical, and a tube like half transparent film 21 sealed at the lower end is housed therewithin, and a mesh-like protecting cover 22 is encircled on the outer part of the film 21.

At the outside of the film 21, a culture media and gas container 23 is formed, and a communication mouth 24 is provided at a side of the sealing case 20 for communicating with the container 23, and a communication mouth 25 is provided at the upper part of the container 20 for communicating with the interior of the film 21.

FIG. 5(A) shows an instrument for reducing this inventive method to practice most easily, where the cells and the media are enclosed in the bag 34 to float them in the cultivating liquid 32 in the container 30 as a glass or plastic bottle, and its mouth is sealed with a pin 31. The bag 34 is, as shown in FIG. 5(B), sealed at a lower part 35 shaped in tube, and is equipped with a rubber plug 36 to which a charging mouth 37 is connected.

FIG. 6 is a whole perspective view showing one example of a rotary cell cultivating device (agitator) to be used for agitation of the floating cells and the media. The numeral 40 is a rotary plate, and 41 is a box where a rotation drive mechanism of the rotary plate 40 is housed.

The rotary plate 40 is inclined appropriately with respect to the horizontal surface, and is furnished with securing means 60 for the cultivating bag at four corners. In the present embodiment, the angle of inclination is 45°.

FIG. 7 shows setting-up of the securing means 60 in detail.

The rotary plate 40 is formed with pin holding holes 40a at the four corners, said holes extending toward the center of the rotary plate 40. The hole 40a is formed with a plurality of arc shaped cutouts 40b for holding the pin 60 at several steps.

The hole 40a is inserted with the pin 61 at its lower part 61b from the upper side of the rotary plate 40, and a securing screw 62 tightens it and the pin 61 is fixed to the rotary plate 40. A flange 61a is positioned about the lower portion of the pin 61, and a pin portion 61b lower than the flange 61a has a diameter to be fitted to a cutout 40b of the pin holding hole 40a and is formed with a screwing groove (not shown) therein.

The securing screw 62 is also formed with a flange 62a, and a portion 62b formed at an end of the screw 62 has a diameter to be fitted to the cutout 40b of the hole 40a. Further a screw 62c is screwed with a groove of the lower pin 61b.

The screw 62 is screwed by the pin 61, and the flanges 61a, 62a tighten the circumference of the hole 40a so as to secure the pin 61 to the rotary plate 40.

When the position of the pin 61 is adjusted, the screw 62 is loosened and the pin 61 is moved in length of the hole 40a, and the lower pin 61 is moved to a desired one of the cutouts 40b and the pin 61 is again secured to the rotary plate 40 by the screw 62.

The pin 61 is slidably mounted thereon with a cylindrical stopper ring 64 having a tightening screw 63a, and if the screw 63a is tightened, the stopper ring 63 may be positioned at any part in length of the pin 61.

FIG. 8 is an outlined view showing a rotating mechanism of the rotary plate 40. Within the box 41, there is secured a plate 49 for attaching the drive part, inclining appropriately (45° in this embodiment). The attaching plate 49 is provided with a motor 48, a speed reduction gear head 42 and a bearing 46. The numeral 43 is a plate for supporting the motor 48.

A shaft is seen connected by a joint 45 between the gear head 42 and the bearing 46. A rotary shaft 44 is pivoted by the bearing 46 and is fixed with a part 47 for carrying the rotary plate 40 by bolts.

A motor control unit 50 is housed therein with a mechanism for controlling rotation of the motor 48 at determined speed. In this embodiment, the rotation speed of the rotary plate 40 may be determined within 0.5 to 10 rpm.

The structure of the securing means 60 of the cultivating bag of this invention and the rotation mechanism of the rotary plate 40 are not limited to the shown ones, but may be varied in response to demands.

As shown in FIG. 9, the rotary cell culture device is carried on and in accordance with an instrument 51 so as to control the angle appropriately to the cells to be cultivated. The agitator rotates the culture device, but may turn it laterally and longitudinally.

FIGS. 10 and 11 explain the shaking operation.

The numeral 70 designates a shaking plate for holding the cell culture device, where a point O is a center of the shaking plate, A and C are points on X-axis, running through the center O, and B and D are points on Y-axis, running through the same. The shaking plate 70 moves on the culture device around the X and Y axes laterally and longitudinally.

FIG. 11 is a side view of the plate 70, showing a condition that the plate 70 is moved around the Y-axis. Points A and C of the plate 70 is moved vertically in reference to height hO of the center O. The maximum width of turning of A and C is expressed with +hA, −hA and +hC, −hC ("+" is the maximum value in a direction higher than hO, and "−" is the maximum value in a direction lower than hO). When moving the plate 70 around the X-axis, the moving widthes of B and D are expressed with +hB, −hB and +hD, −hD.

With respect to a first embodiment of the shaking plate 70, while the plate 70 once moves vertically around the X-axis (actually, the X-axis moves slightly in circle, cf FIG. 12), the plate 70 once moves vertically around the Y-axis (actually, the Y-axis also slightly moves in a circle.

A reference will be made to a case that the vertical and simultaneous movements of the plate 70 around the X- and Y-axes are repeated periodically. The cycles of hO and hA, hB, hC, hD will be expressed with a formula (1).

$$
\begin{aligned}
1 \quad & hA = \cos\omega t \\
2 \quad & hB = \cos(\omega t - \pi/2) \\
3 \quad & hC = \cos(\omega t - \pi) \\
4 \quad & hD = \cos(\omega t - 3/2\pi) \\
5 \quad & h0 = 0
\end{aligned}
\quad (1)
$$

Herein, h is height, t is time, and $\omega$ is angular velocity. The angular velocity is expressed with a following formula $\omega = 2\pi f$ (f is vibration number).

At this time, the positioning relationship of ho and hA, hb, hC, hD are changed periodically as shown in a formula (2).

$$
\begin{aligned}
6 \quad & hA > h0,\ hC < h0,\ hB = h0,\ hD = h0 \\
7 \quad & hA = h0,\ hC = h0,\ hB > h0,\ hD < h0 \\
8 \quad & hA < h0,\ hC > h0,\ hB = h0,\ hD = h0 \\
9 \quad & hA = h0,\ hC = h0,\ hB < h0,\ hD > h0
\end{aligned}
\quad (2)
$$

Steps 6, 7, 8, 9 of the formula correspond to t1, t2, t3, t4 of FIG. 12.

FIG. 12 shows periodical changes of hA, hB, hC, hD in time. It is seen that the vertical movements of A, B, C, D of the plate 70 are in the relations having phases. The once vertical movement of the plate 70, which will be explained with an example of B of FIG. 12, means that the height hB of the point B moves vertically in one cycle of hO→→hB→hO→−hB→hO.

FIGS. 14 to 17 show movements of the shaking plate 70 following this shaking cycle.

(a) In FIG. 14, the point A in the X-axis is at the height of +hA, and the point C is at the height of −hC. The points B and D in the Y-axis are at the same height as hO (t1 time in FIG. 12).

The plate 70 begins to turn around the Y-axis and the points A, C start to move to the same height as hO, and at the same time B starts to +hB about the X-axis, and D starts to −hD (t1+Δt time in FIG. 12).

(b) Subsequently, as shown in FIG. 15, B is at the height of +hB, and D is at the height of −hD, and A and C are at the same height of hO (t2 in the same).

The turning plate 70 starts to turn about the X-axis, and B, D move to the same height of hO, and concurrently A to −hA, and C to −hC (t2+t time in same).

(c) As shown in FIG. 16, the point C comes to the height of hC, the point A to −hA, and B, D to the same height of hO (t3 time in same).

The plate 70 starts to turn about the Y-axis, and gradually the points A, C come to the height of hO, and D to +hD, and B to −hB.

(d) As shown in FIG. 17, the point D becomes the height of +hD, and A, C to hO (t4 time).

After then, B, D become hO, and the point A to +hA, and C to −hC (t4+Δt time), and again they return to the (a) condition and repeat the (a) to (d) conditions.

Turning System I

FIG. 13 shows one example of a device for moving the shaking plate carrying the cell culture container in accordance with the above mentioned principle. A securing means for a culture container 71 is the same as that of FIG. 7. The center O of a shaking plate 70 is pivoted at a free angle by means of the link ball 79a at an end of a pole 78 held by a box 74. Shaking plate 70 is driven by a drive mechanism 73. The box 74 is housed therein with a motor 75, gears 76a, 76b, 76c. These gears are in mesh each other, and the gear 76b is connected to the motor 75 via a joint 77. Another gear 76a is fixed with a link 80, and the gear 76c is fixed with a link 81. The link 80 is pivoted with one end of the push bar 82, and the other end of which is pivoted on the x-axis (or Y-axis) in the plate 70 via the link ball 79b. Similarly, the link 81 is pivoted with one end of the push bar 83, and the other end of which is pivoted on the Y-axis (or X-axis) in the plate 70 via the link ball 79c.

Actuation of the shaking device shown in FIG. 13 will be explained in comparison with the shaking of said plate 70 with reference to FIGS. 18 to 21.

Changings of the shaking device in FIGS. 18 to 21 correspond to those of FIGS. 14 to 17, where (A) are the outlines of rear side of FIG. 13, and (B) are the right side views of (A).

(a') A connection 85 between the link 80 and the push bar 82 is at the position (P1), so that the push bar 82 moves upwardly the point A of the plate 70 to +hA, and the point C is moved down to −hC. At this time, since a connection 86 (pivot portion) between the link 81 and the push bar 83 is at the position (Q4), the points B, D of the plate 70 are at the same position as the center O (FIG. 18).

(b') When the links 80, 81 turn 45° counterclockwise, the connection 85 between the link 80 and the push bar 83 moves to the position (P2), and the points A, C of the plate 70 are at the same height as the point O.

Since the connection 86 is at the position (Q1) at this time, the point B of the plate 70 is pushed upwardly to the height +hB, and the point D is moved down to the height −hD (FIG. 19).

(c') When the links 80, 81 turn further 45°, the connection 85 moves to the position (P3), so that the point A of the plate 70 is pulled down to the height of −hA, and the point C is moved upward to the height of +hC. Since the connection 86 is at the position (Q2) at this time, the points B, D of the plate 70 are at the same height as the point O (FIG. 20).

(d') When the links 80, 81 are rotated 45° counterclockwise, the connection 85 is at the position of (P4), so that the points A, C of the plate 70 are at the same position as the point O.

Then, since the connection 86 is at the position of (Q3), the point B of the plate 70 is moved down to the height of −hB, and the point D is moved upward to the height of +hD (FIG. 21).

Further, when the links 80, 81 are rotated 45° counterclockwise, the condition is returned to the above mentioned (a') state and the (a') to (d') states are repeated.

Turning system II

A further reference will be made to a case that the shaking plate is actuated vertically around the X- and Y-axes n times irregularly, thereby to enable to select the relation between hO and hA, hB, hC, hD.

FIG. 22 is a front view of the shaking device for practising the present example, and FIG. 23 is a side view of FIG. 22. The shaking plate 70 has a center O which is pivoted at a free angle to a pole 91a by means of a link ball 90a. Push bars 91, 92 are for the plate 70, and the former is pivoted on the X-axis, and the latter is pivoted on the Y-axis via link balls 90b, 90c.

The other end of the push bar 91 is turnably provided at the end of a rack 93 and the other end of the push bar 92 is turnably provided to a rack 94. The rack 93 is moved by a pinion gear 96 to be rotated by a motor 95. The rack 94 is moved by a pinion gear 98 to be rotated by a motor 97.

A device 99 controls rotation speed and rotating direction of the motors 95, 97. By the control device, the motors 95, 97 may be driven independently or concurrently.

(a") At first, the heights hA, hB, hC, hD of the points A, B, C, D of the shaking plate 70 are at the same height as hO of the point O (t1 time in FIG. 24).

When the rack 93 is advanced by driving of the motor 95, the push bar 91 pushes up the plate 70. Thereby the plate 70 starts to turn about the Y-axis, and the point A moves vertically to +hA and the point C of −hC (t1+Δt time in FIG. 24).

(b") After the point A comes to the height of +hA, and the point C to the height −hC (t2 time in FIG. 24), the rack 93 is moved back by reversing the motor 95, and the push bar 91 pulls down the plate 70, and gradually the points A, C start to move to the same height as hO (t2+Δt time in FIG. 24). Then, the points B, D are always at the same height as hO until t1 to t2+Δt time.

(c") After the points A, B, C, D again return to the same height as hO (t3 time in FIG. 24), the rack 94 is advanced by the motor 97, and the push bar 92 pushes the plate 70. Thereby the plate 70 starts to turn about the X-axis, and gradually the point B starts to move vertically to +hB, and the point D to −hD (t3+Δt time in FIG. 24).

(d") After the point B comes to +hB, and the point D to −hD (t4 time in FIG. 24), the rack 94 is moved back by reversing the motor 97, and the push bar 92 pulls down the plate 70. Therefore the plate 70 starts to turn around the X-axis, and gradually the points B, D move vertically to the same height as hO (t4+Δt time in FIG. 24). At this time, the points A, C are at the same height as hO until t3 to t4+Δt.

(e") The points A, B, C, D return to the same height as hO, and carry out the turnings as repeating the following actuations.

At t5 time and t5+Δt time, the actuation of (c"), at t6 time and t6+Δt time, the actuation of (d"), at t7 time and t7+Δt time, the actuation of (a"), and at t8 time and t8+Δt time, the actuation of (b").

Thus, in this example, the plate 70 turns while repeating alternately vertical movements of ½ times about the X-axis and ½ times about the Y-axis.

According to the device of FIGS. 22 and 23, the above mentioned turning system I may be practised.

A following reference will be made to the shaking thereof.

(f') At first the points A, B, C, B are at the same height as hO (time t9).

When the motor 97 is reversely rotated to move back the rack 94, the point B of the plate 70 is moved toward −hB around the X-axis, and the point D toward +hD (t9+Δt time in FIG. 24).

(g") After the point B becomes the position of —hB and the point D becomes +hD (t10 time in the same), the motor 95 is driven and the rack 93 is advanced to push up the plate 70, and the plate 70 is pulled down by the motor 97 via the push bar 92. From t10+Δt time to t14 time, the plate may be turned in the same way as turning from t4+Δt time to t8 time.

Further in the present embodiment, it is possible to push up or pull down the shaking plate 70 at the same time via the push bars 91, 92 by rotating the motor 95 normally or reversely.

FIG. 25 shows that the shaking plate 70 in FIG. 13 is housed within a sealed container 100, and temperature therein is controlled to be optimum to the cell cultivating condition.

A further reference will be made to a sequence of cultivating the cells by means of the culture device shown in FIG. 2 and the rotation device of FIG. 6.

An outer bag of the culture container used in this example is made of polyvinyl chloride. The sheet thickness of 0.4 mm, and the capacity is 4,000 ml in total of the exterior liquid being 2,000 ml and the air being about 2,000 ml. The inner bag 3 is made of re-generated cellulose. The film thickness is 20 μm, the molecular weight 10,000 and the capacity is 1000 ml in total of the interior liquid being 500 ml and the air being about 500 ml. In the present operating example, an explanation will be made in reference to the cultivation of human lymphocytes. The invention is also available especially as the high density cultivation of cell line derived from the blood such as mouse hybridoma.

(I) Washing of culture bag

The inner bag 3 is coated with glycerine against drying. So the washing is required with a physiological salt solution.

As shown in FIG. 26, a communication tube 111 is connected to a bag 110 holding the physiological salt solution at one end, and connected to an inner liquid handling mouth 4 (communication mouth) at the other end. The communication tube 111 has liquid lead needles 112, 113, and a clamp 114 at a middle part. The clamp 114 is at first closed, and opened after having connected the handling mouth 4 and the bag 110, thereby to pour the physiological salt solution about 500 ml due to a head.

The clamp 114 is closed, and the connection tube 111 is taken off from the bag 110, after which, two parts around the handling opening 4 are knotted to seal and unnecessary parts are cut off.

The inner bag 3 is confirmed about leaking, and the physiological salt solution is charged about 2000 ml into the outer bag 1 in the same way as said above. FIG. 27 shows that after the salt solution is supplied into the outer bag 1, a communication tube 111a is sealed at 115, 115a. For the exterior handling opening 2 (communication opening), one without a protector 2a is used first.

The culture bag is provided on a rotary agitator shown in FIG. 6, and rotated 4 to 5 rpm for about 15 minutes.

(II) Pouring of lymphocytes suspended in media (interior liquid) and culture media (exterior liquid)

(1) Discharge of washing liquid

The culture bag is removed from the rotary agitator, and the communication tube 111a is taken off from the exterior liquid handling mouth 2, and a new communication tube (clamp is closed) is connected. The clamp of the communication tube is opened, and the washing liquid within the outer bag 1 is discharged due to the head, after which, the communication tube is firmly knotted twice to seal and unnecessary parts are cut off.

After then, the inner bag 3 is confirmed about leaking, and the washing liquid within the inner bag 3 is discharged in the same way as said above, and the communication tube is sealed and unnecessary parts are cut off.

(2) Charging of interior liquid

Lymphocytes suspended in medium is charged into the inner bag 3 within a clean bench.

The lymphocytes suspended in medium is charged in a following procedure.

The communication tube 111 is removed from the interior liquid handling mouth 4, and an instrument 120 for pouring cell suspended liquid is connected as shown in FIG. 28 in a manner that a leading tube 122 is connected to a funnel 121, and a needle 123 is attached to said tube 122.

After the needle 123 is pierced into the mouth 4, the lymphocytes suspended in medium is poured into the interior bag 3 due to the head.

After pouring the lymphocytes suspended media, the pouring instrument 120 is taken off, and an adaptor 130 shown in FIG. 29 is connected, which is composed by a cap 132 having a rubber plug at a rear portion of a liquid lead needle 131.

The adapter 130 is connected with an instrument 140 for supplying a sterilized air as shown in FIG. 30, which is composed by connecting in order a disposable syringe 144, a three-way stopcock 143, a disposable membrane filter 142 and a disposable needle 141.

After piercing the disposable needle 141 into the rubber plug of an operating adaptor 130, the sterilized air is supplied by piston action of a syringe 144 and switching of the three-way stopcock 143 so that the inner bag 3 is effected with tension. The amount of the sterilized air is not especially determined. After supplying the sterilized air, the instrument 140 is removed.

(3) Pouring of the exterior liquid

As shown in FIG. 31, The culture media bag 150 which has been in advance prepared, is connected with one needle 112b of the connection tube 111b of the same structure as said above, and the communication tube is removed from the exterior handling mouth 2 of the outer bag, and the other needle 113b is connected to said opening 2. After then, the clamp 114b is opened, and the exterior liquid is poured due to the head.

Then, the communication tube 111b is taken off from the mouth 2, and connected with an adaptor 130 of the same structure as said above.

A sterilized filter 142 and a disposable needle 141 of the sterilized air supplying instrument 140 are exchanged with new ones and the sterilized air is supplied into the outer bag 1 in the same manner as into the inner bag 3 so as to give the tension to the outer bag 1. The amount of the sterilized air is not determined as said.

(III) Starting of cultivation

A rotary agitator as shown in FIG. 6 is installed in a thermostatic chamber set at 37° C. or an incubator, and the culture bag is set as shown in FIG. 32.

The culture bag is provided on the rotary plate 40 by loosening a screw 63a of a tightening means 60 to remove a stopper ring 63 from a pin 61, mounting each of attaching holes 7 onto each of the pins 61, inserting the stopper ring 63 into the pins 61, tightening the screws 63a and securing the ring 63 to the pin 61. Thus, each of corners of the outer bag 1 is fixed to each of the corners of the rotary plate 40.

If the culture bag had any slack, an inherent shape could not be maintained, and smooth agitation could not be made. Therefore, the culture bag should be provided in tension.

The culture bag is given tension by loosening a screw 62 of a pin 61, moving the pin 61 along the hole 40a to a proper position of the cutout 40b, and fixing the pin 61 by the screw 62. The same operation is made to other remaining positions to give tension over the culture bag.

When the culture bag is attached to the rotary plate 40, the rotation speed is determined, and the motor 41 is driven. Since the rotary plate 40 is rotated while being tilted with respect to the horizontal surface, the culture bag is periodically reversed at the top and the bottom, so that the interior liquid and the exterior liquid are agitated within the sealed bags. Both liquid contact each other through the semi-permeable film as and the media in the exterior liquid moves into the interior liquid due to diffusion phenomena.

The rotation speed of the plate 40 is generally 4 to 5 rpm. The cultivation by this device is undertaken within the thermostatic chamber or the incubator the temperature of which has been set suitably to the cultivation.

The culture bag is attached to the rotary plate 40, and the latter is rotated 4 to 5 rpm for doing cultivation.

(IV) Exchange of culture media (exterior liquid)

An exchanging period is judged when the exterior liquid becomes yellow. It is convenient to divide the much controlled culture media into culture bags.

When the culture media are exchanged, the rotation of the rotary agitator is stopped and the culture bag is removed. Then, the handling opening 2 of a non-used exterior liquid is connected with a communication tube (clamp is closed) of the same structure as shown in FIG. 26, and the clamp is opened to discharge the exterior liquid due to the head.

After discharging the exterior liquid, the clamp is closed, and a culture bag which has been in advance produced is connected with another communication tube (clamp is closed), after which, the communication tube connected to the opening 2 is taken off and connected with the communication bag of said culture bag, and at the same time, the clamp is opened to charge the exterior liquid due to the head.

When the exterior liquid has been completed in pouring, the clamp is closed, and the communication tube is taken off from the culture bag and is knotted twice and firmly sealed, and unnecessary parts are cut off. If the outer bag is lacked in tension, the sterilized air is supplied in the same way as said above.

The culture bag is fixed to the rotary agitator, and the cultivation is again performed.

(V) Finishing of the cultivation and yielding of lymphocytes suspended in media (interior liquid)

Having completed the cultivation, the culture bag is removed from the rotary agitator, and a yielding bag 170 as shown in FIG. 33 is prepared.

The yielding bag 170 is connected with a leading tube 171, and a liquid lead needle 172 is provided at its end portion. The lead tube 171 is knotted moderately as shown in FIG. 33 nearly the bag and a loop 173 is made in advance. The operation adaptor is taken off from the handling opening 4 of the interior liquid, and the needle 172 of the yielding bag 170 is connected thereto, and the interior liquid is yielded into the yielding bag 170 due to the head via the leading tube 171.

The loop 173 of the tube 171 is, after yielding, firmly knotted, and the needle 172 is removed from the handling opening 4. Another knot is made nearly said knot, and is sealed. Unnecessary parts are cut off.

The above mentioned culture bag, media bag, yielding bag, communication tube, operation adapter, cell pouring instrument, and sterilized air supplying instrument are all disposable products made of plastics.

The following will refer to examples of cultivating cells by using the devices of the invention.

EXAMPLE 1

The culture liquid (RPMI 1640 500 ml) containing human lymphocytes, interleukin-2 (called as "IL-2" hereinafter) and +human AB serum (20%) was sealed into the inner bag 3 of the culture device (pore size: 24 Å). The culture liquid (RPMI 1640: 2000 ml) and the air (2000 ml) were supplied into the outer bag.

The culture instrument was fixed to the rotary plate 40 of the agitator (rotation angle: 30°), and the leading of the LAK cell (lumphokine-activated killer) was carried out in an incubator. During leading, the culture liquid was exchanged from another opening.

Changings of the activated killer of LAK cell according to the invention was compared with the conventional method (roller bottle), and shown in FIG. 34, where a vertical axis if the activated killer and the lateral axis is culturing days, and the solid line shows the present invention and the dotted line shows the prior art.

The activated killer was recognized in increasing for 16 days in the invention and the prior art. The activated killer was measured by ATP method.

The comparison between the invention and the prior art is shown in Table 1. According to the invention, in comparison with the prior art where the culture liquid and the lymphocetyes are mixed, the using amount of the precious IL-2 of the invention is 1000 $\mu$, while that of the prior art is 2500 $\mu$. The amount used of the human AB serum of the invention is 100 ml, while that of the prior art is 1000 ml. Thus, although the invention largely decreased the amount used, the activated killer was equivalent in the invention and the prior art. If using the disposable products as said above, then steriling handling could be performed easier than for the conventional techniques.

TABLE 1

| Comparisons in cultivation of lymphocytes of $1.0 \times 10^{10}$ | | |
|---|---|---|
| | Prior Art | Invention |
| rIL-2 concentration | 0.5 $\mu$/ml | 2.0 $\mu$/ml |
| Cell concentration during cultivation | $2.0 \times 10^6$/ml | $2.0 \times 10^7$/ml |
| Required amount of IL-2 | 2500$\mu$ | 1000$\mu$ |
| Required amount of culture media | 5.0 l | Amount in half transparent film: 0.5 l Amount outside half transparent film: 6 l |
| Cultivating days | 6 days | 6 days |

TABLE 1-continued

Comparisons in cultivation of lymphocytes of $1.0 \times 10^{10}$

|  | Prior Art | Invention |
|---|---|---|
| Required amount of AB serum | 1000 ml | 100 ml |
| Cultivating container | Five of rollor bottles of 2,0 capacity | One cultivating bag |
| Instrument | Bottle roller | Agitator |
| Cultivating place | Exclusive incubator | Incubator of $600 \times 600 \times 600$ mm |

EXAMPLE 2

The culture liquid (Eagle's MEM) containing the air and Raji cell and FCS were sealed in the inner bag 3 of the culture container and the culture liquid (Eagle's MEM) and the air were supplied into the outer bag 3. The culture container is fixed to the rotary plate 40, and the cultivation was done by the incubator.

The increasing curves of Raji cell according to the invention and the conventional method (flask cultivation) are shown in FIG. 35, where the vertical axis is concentration of cell and the lateral axis is culture days, and the solid line is the invention and the dotted line is the prior art.

The present inventive method and the conventional method began the cultivations at cell concentration of $50/mm^3$. When the latter reached the cell concentration of $455/mm^3$ in four days of the cultivation, thereafter it went down, but the invention continued the increasing cell concentration of $2060/mm^3$ after seven days of the cultivation.

EXAMPLE 3

The air and the culture liquid (NS-1) containing the mouse hybridoma and FCS were sealed into the inner bag 3 of said culture container, and the air and the culture liquid (NS-1) were seale into the outer bag. The culture container was fixed to the rotary plate 40 of the agitator and the cultivation was done in the incubator. The increasing curves of the hybrimoda by the invention and the prior art are shown in FIG. 36.

The conventional method reached the cell concentration of $1000/mm^3$ in the four cultivating days, and when down thereafter, but the invention continued to increase up to the cell concentration of $10000/mm^3$ in the six cultivating days.

Further investigations were made in developments of Examples 1 to 3, and excellent results are shown in Table 2, where the data concerning the cultivation in flask of the prior art are shown for comparison.

TABLE 2

| Cultivating condition | Kind of cell | | | | |
|---|---|---|---|---|---|
|  | Mouse Hybridoma (NS-1 Mother cell) | | | | |
| Kind of cultivation | With FCS | With FCS | Completely serum-free | Completely serum-free | Raji cell With FCS |
| Components of interior medium | 20% FCS + NS-1 | 20% FCS + NS-1 | 2% BSA + NYSF-404 + 0.01% Trypsin | 2% BSA + NYSF-404 + 0.01% Trypsin | 20% FCS + Eagle's MEM |
| Volume of interior medium | 5 ml | 5 ml | 5 ml | 5 ml | 5 ml |
| Number of cells at state of cultivation | $2.0 \times 10^5/ml$ | $2.0 \times 10^5/ml$ | $2.0 \times 10^5/ml$ | $2.0 \times 10^5/ml$ | $2.0 \times 10^5/ml$ |
| Components of exterior medium | NS-1 | NYSF-404 (No insulin, BSA, Transferrin) | NYSF-404 (No insulin, BSA, Transferrin) | NYSF-404 (No insulin, BSA, Transferrin) | Eagle's MEM |
| Period of cultivation | 9 days | 7 days | 6 days | 6 days | 5 days |
| Cell concentration at the end of cultivation ($10^7/ml$) | 1.0–1.3 | 1.3–1.6 | 1.5–2.0 | 2.0–3.0 | 1.00–1.30 |
| Gross volume of exterior medium | 1.0–1.2 l | 1.0–1.2 l | 1.0–1.2 l | 1.0–1.2 l | 1.0–1.4 l |
| Comparison data: Cultivation by conventional flask methods Flask media | 20% FCS + NS-1 | 20% FCS + NS-1 | NYSF-404 (completely SERUM-FREE) | NYSF-404 (Completely SERUM-FREE) | 10% FCS + Eagle's MEM |
| Upper limit of cultivation using flask ($10^6/ml$) | 0.7–0.8 | 0.7–0.8 | 0.6–0.7 | 0.6–0.7 | 0.4–0.6 |
| Increased density of CR tissue cell vs flask | 14–16 × | 18–20 × | 25–28 × | 33–43 × | 25–32 × |
| Increased density of monoclonal antibodies vs Standard methods | 60–120 × | 120 × | 120 × | 120–240 × |  |
| Cells in flask Remarks | Epith | Epith | Lym | Lym *E-NYSF404 (enriched NYSF-404) | Lym |

| Cultivating condition | Kind of cell | | | |
|---|---|---|---|---|
|  | Lymphocyte (Human) | | | |
| Kind of | LAK | PHA | PHA BLAST | HeLa |

TABLE 2-continued

| cultivation | Induction | Rejuvenation | Cultivation | With FCS | With FCS |
|---|---|---|---|---|---|
| Components of interior medium | 5 u/m rIL-2 + 20% AB serum + RPMI 1640 | 1% PHA-H + 10% FCS + RPMI 1640 | 5 u/m rIL-2 + 10% FCS + RPMI 1640 | 10% FCS + Eagle's MEM | 10% FCS + Eagle's MEM + 0.1% Trypsin |
| Volume of interior medium | 500 ml | 5 ml | 5 ml | 5 ml | 5 ml |
| Number of cells at state of cultivation | $2.0 \times 10^7$/ml | $1.0 \times 10^6$/ml | $1.0 \times 10^6$/ml | $2.0 \times 10^5$/ml | $2.0 \times 10^5$/ml |
| Components of exterior medium | RPMI 1640 | RPMI 1640 | RPMI 1640 + 0.0032% | Eagle's MEM | Eagle's MEM |
| Period of cultivation | 6 days | 7 days | 7 days | 5 days | 8 days |
| Cell concentration at the end of cultivation ($10^7$/ml) | 0.9–1.4 | 0.6–1.6 | 0.8–1.2 | 0.2–0.4 | 0.8–1.2 |
| Gross volume of exterior medium | 8.0–12.0 l | 0.1–0.2 l | 0.4–0.6 l | 0.8–1.0 l | 0.8–1.2 l |
| Comparison data: Cultivation by conventional flask methods Flask media | 20% AB serum + 0.5 u/m rIL-2 + RPMI 1640 | 10% FCS + 1% PHA-M + RPMI 1640 | 10% FCS + 5 u/m rIL-2 + RPMI 1640 | 10% FCS + Eagle's MEM | 10% FCS + Eagle's MEM |
| Upper limit of cultivation using flask ($10^6$/ml) | 2.0–2.5 | 1.0–2.0 | 1.0–2.0 | 0.2–0.4 | 0.2–0.4 |
| Increased density of CR tissue cell vs flask | 8–10 × | 3–10 × | 5–8 × | 10–20 × | 30–40 × |
| Increased density of monoclonal antibodies vs Standard methods | | Not test | | | |
| Cells in flask | Lym | Lym Agricated | Lym | Epith | Epith |
| Remarks | | | | | |

| | Cultivating condition | Kind of cell | | | |
|---|---|---|---|---|---|
| | | HeLa | | | |
| | Kind of cultivation | Completely SERUM-FREE | MDT-4 With FCS | SU-1 With FCS | HBS With FCS |
| | Components of interior medium | 2% BSA + NYSF-404 + 0.05% Trypsin | 20% FCS + RPMI 1640 | 20% FCS + McCoy's 5A | 20% FCS + RPMI 1640 |
| | Volume of interior medium | 5 ml | 5 ml | 5 ml | 5 ml |
| | Number of cells at state of cultivation | $2.0 \times 10^5$/ml | $2.0 \times 10^5$/ml | $4.0 \times 10^5$/ml | $3.0 \times 10^5$/ml |
| | Components of exterior medium | NYSF-404, (No insulin, BSA, Transferrin | RPMI 1640 | McCoy's 5A | RPMI 1640 |
| | Period of cultivation | 8 days | 9 days | 4 days | 7 days |
| | Cell concentration at the end of cultivation ($10^7$/ml) | 0.6–1.0 | 1.2–1.4 | 1.0–1.2 | 1.4–1.6 |
| | Gross volume of exterior medium | 0.4–0.8 l | 0.8–1.2 l | 0.4–0.8 l | 0.8–1.0 l |
| | Comparison data: Cultivation by conventional flask methods Flask media | NYSF-404 (Completely SERUM-FREE | 10% FCS + RPMI 1640 | 10% FCS + McCoy's 5A | 10% FCS + RPMI 1640 |
| | Upper limit of cultivation using flask ($10^6$/ml) | 0.2–0.4 | 1.0–1.2 | 0.3–0.5 | 1.0–1.2 |
| | Increased density of CR tissue cell vs flask | 25–30 × | 12–13 × | 24–33 × | 13–14 × |
| | Increased density of monoclonal antibodies vs Standard methods | | | | |
| | Cells in flask Remarks | Epith | Lymp | Lymp *SU-1 Derived | Lymp |

TABLE 2-continued

|  | from Ovarian Carcinoma |
| --- | --- |

CR Tissue: Notes
(1) FCS = Fetal Calf Serum
(2) PHA = Phytohemaglutinin Rejuvenation
(3) BSA = Bovine Serum Albumin
(4) Epith = Epithelial - like cell
(5) Lymph = Lymphoblast - like cell
(6) E-NYSF-404 = Enriched NYSF-404
(7) SU-1 = Derived from Ovarian Carcinoma As having mentioned above, according to the present invention, following excellent effects could be brought about. (1) In comparison with the prior art, effective and economical cultivation is possible. Actually, for example, in Example 1, the amounts used of IL-2 and the human AB serum may be largely decreased, and in cell cultivations in Examples 2 and 3 and Table 2, the high concentration is possible in comparison with the prior art. It is possible to culture the cells by changing, if necessary, the media in the semi-permeable film container and the components of the media outside of the film.

(2) The cultivation within the sealing is possible, and since the media liquid is not circulated as is done in the conventional hollow membrane, sterilized operation may be easily made.

(3) The cultivation is possible with narrow spaces and small scaled instruments in comparison with the rotary cultivation by the conventional roller bottle. Further, as in the cultivation with the hollow membrane, any complicated system is not required, and much condensed cultivation is possible.

(4) The cell to be cultivated and the culture media are sealed in the different containers. The charging and yielding of the cells, the exchanging of the culture media, and the supplying of the sterilized air are carried out by an easy one touch connection of the operating instrument.

(5) By using each of the above instruments, the cell yielding and exchange of the culture media may be carried out under the sterilized condition.

(6) In comparison with the rotary cultivation by the conventional roller bottle, nutrition passes to the cell side through the half transparent film, and by exchanging the culture media it is possible to cultivate the cell in the half transparent film at high concentration.

(7) Since the cells and the culture media are moderately agitated, the component of the cell is uniformly dispersed, and the cells do not attach to the wall of the container or cause condensation, and the high yield may be obtained. In addition, the cultivation is carried out while rotating or shaking the culture container, so that much cultivation is possible in spite of the small area of the film in comparison to the conventional culture container of the hollow membrane.

What is claimed is:

1. An apparatus for floating animal cells in a culture liquid comprising: a culture container, wherein said culture container comprises;

an outer bag means for sealing a culture liquid and a volume of gas, said outer bag means comprising a pair of plastic sheets sealed at circumferential parts thereof and plastic tubes secured between the sealed circumferential parts for injecting culture liquid and a volume of gas, an inner bag means for supporting animal cells to be cultured under a condition wherein animal cells float in a culture liquid, said inner bag means comprising a pair of semipermeable film sheets sealed at circumferential parts thereof, said film sheets having pores of a sufficient size so as to prohibit cells within the inner bag from passing therethrough but allowing culture liquid and air to pass through it, and a plastic tube secured between the sealed circumferential parts of said inner bag means and said outer bag means for injecting a cell suspension, and a protective plastic mesh surrounding said inner bag means so as to prevent said inner bag means from contacting said outer bag means.

2. The apparatus as defined in claim 1, further comprising a rotating means which includes a rotating plate for holding the culture container and a drive mechanism for rotating the rotating plate, said rotating plate being oblique and including fixing means for fixing a plurality of said circumferential parts of said outer bag means to the rotating plate and wherein said fixing means is displaceable for imparting tension to the culture container.

3. The apparatus as defined in claim 1, further comprising a shaking means which includes: a shaking plate for holding the culture container, said shaking plate having a center point where a first axis and a second axis intersect perpendicular to one another; support means for supporting said shaking plate; and drive means for moving the shaking plate, said support means including a first connecting mechanism for moving the shaking plate about said first axis and a second connecting mechanism for moving the shaking plate about said second axis, said first connecting mechanism and said second connecting mechanism being connected to said drive means so as to oscillate said plate alternately about said first axis and said second axis, said shaking plate including fixing means for fixing a plurality of said circumferential parts of said outer bag means to said shaking plate and wherein said fixing means is displaceable for imparting tension to the culture container.

4. The apparatus as claimed in claim 3, wherein said first connecting mechanism and said second connecting mechanism each comprise a rotating plate connected to said drive means so as to rotate about its center and a connecting member pivotally attached to both said rotating plate radial to said center and said shaking plate.

5. The apparatus as claimed in claim 3, where said first connecting mechanism and said second connecting mechanism each comprise a rod connected to said drive means so as to oscillate along its length and a connecting member pivotally attached to both said rod and said shaking plate.

6. The apparatus as claimed in claim 2, wherein said culture container further comprises holes formed in said circumferential parts of said outer bag means and said fixing means further comprises a plurality of oblong holes in said rotating plate, pins inserted in said oblong holes so as to attach said culture container by said circumferential holes, means for tightening the culture container to said pins, and means for tightening said pins to said rotating plate.

7. The apparatus as claimed in claim 3, wherein said culture container further comprises holes formed in said circumferential parts of said outer bag means and said fixing means further comprises a plurality of oblong holes in said rotating plate, pins inserted in said oblong holes so as to attach said culture container by said circumferential holes, means for tightening the culture container to said pins, and means for tightening said pins to said shaking plate.

8. The apparatus as claimed in claim 1, wherein said culture container further comprises holes formed in said circumferential parts of said outer bag means so as to enable the attachment of said culture container to one of a rotating device and a shaking device.

* * * * *